United States Patent
Burty et al.

(10) Patent No.: US 9,902,934 B2
(45) Date of Patent: Feb. 27, 2018

(54) HUMAN KERATINOCYTES PTCH1 CELL LINE

(71) Applicants: GALDERMA RESEARCH & DEVELOPMENT, Biot (FR); CNRS, Paris (FR)

(72) Inventors: Elodie Burty, Sourcieux-les-Mines (FR); Thierry Magnaldo, Nice (FR); Yannick Gache, Nice (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 48 days.

(21) Appl. No.: 14/346,872

(22) PCT Filed: Sep. 24, 2012

(86) PCT No.: PCT/EP2012/068775
§ 371 (c)(1),
(2) Date: Mar. 24, 2014

(87) PCT Pub. No.: WO2013/041724
PCT Pub. Date: Mar. 28, 2013

(65) Prior Publication Data
US 2014/0234852 A1    Aug. 21, 2014

Related U.S. Application Data

(60) Provisional application No. 61/538,594, filed on Sep. 23, 2011.

(51) Int. Cl.
*C12N 5/071* (2010.01)
*G01N 33/50* (2006.01)

(52) U.S. Cl.
CPC ....... *C12N 5/0629* (2013.01); *G01N 33/5011* (2013.01); *C12N 2510/04* (2013.01); *G01N 2500/10* (2013.01)

(58) Field of Classification Search
None
See application file for complete search history.

(56) References Cited

PUBLICATIONS

Ikram, Mohammed S. Analysis of Sonic Hedgehog signaling pathway gene expression in Basal Cell Carcinoma and in GL1 induced systems. May 2007. Centre for Cutaneous Research St Batholomew's and The Royal London School of Medicine and Dentistry Queen Mary's College University of London. 348 pages.*
Simbulan-Rosenthal et al. HPV-16 E6/7 immortalization sensitizes human keratinocytes to ultraviolet B by altering the pathway from caspase-8 to caspase-9-dependent apoptosis. Jul. 5, 2002. Journal of Biological Chemistry. vol. 277, No. 27, pp. 24709-24716.*

* cited by examiner

*Primary Examiner* — Channing S Mahatan
(74) *Attorney, Agent, or Firm* — Dentons US LLP

(57) ABSTRACT

A cellular model is described for targeting dysregulation or inappropriate activation of the Sonic Hedgehog/Patched (SHH/PTCH) pathway. Also described, is a screening method using this cellular model to screen for pharmacological compounds that can treat or prevent skin cancer and, in particular, Basal Cell Carinoma (BCC) lesions.

11 Claims, 3 Drawing Sheets

SEQUENCE LISTING

```
<160> NUMBER OF SEQ ID NOS: 1

<210> SEQ ID NO 1
<211> LENGTH: 9
<212> TYPE: DNA
<213> ORGANISM: Homo sapiens

<400> SEQUENCE: 1 gaccaccca                                                              9
```

HUMAN KERATINOCYTES PTCH1 CELL LINE

CROSS-REFERENCE TO PRIOR APPLICATIONS

Figure 1:

This application is a National Stage of PCT/EP2012/068775, filed Sep. 24, 2012, and designating the United States (published in English on Mar. 28, 2013, as WO 2013/041724 A1), which claims priority under 35 U.S.C. §119 to U.S. Provisional Patent Application No. 61/538,594, filed Sep. 23, 2011, each hereby expressly incorporated by reference in its entirety and each assigned to the assignee hereof.

SEQUENCE LISTING

The instant application contains a Sequence Listing which has been submitted electronically in ASCII format and is hereby incorporated by reference in its entirety. Said ASCII copy, created on Jan. 29, 2015, is named Sequence_Listing20009402-1473_ST25.txt and is 490 bytes in size.

The present invention is in the domain of pharmacy and more specifically in skin cancer area and particular for Basal Cell Carcinoma (BCC). The present invention provides a cellular model targeting the Sonic Hedgehog/Patched (SHH/PTCH) pathway dysregulation or inappropriately activated as well as screening method using this cellular model to screen pharmacological compounds able to treat or prevent BCC lesions.

The Hedgehog pathway is normally active during embryonic development and plays a central role in cell differentiation and proliferation.

Inappropriate activation or dysregulation of the Hedgehog pathway is believed to play a critical role in the proliferation and survival of certain cancer cells, including in basal cell carcinoma and medulloblastoma.

Known pathway-activating mutations include those that impair the ability of PTCH, a transporter-like Hh receptor, to restrain Smoothened (SMO) activation of transcriptional targets via the GLI family of latent transcription factors.

Binding of Hh ligand to PTCH is functionally equivalent to genetic loss of PTCH, in that pathway activation by either requires activity of SMO, a sevenpass transmembrane protein that binds to and is inactivated by the pathway antagonist, cyclopamine.

The implication of PATCHED pathway activation in several cancer conditions, most notably in BCCs, has motivated much effort to set up experimental systems to assess the inhibitory activity of small molecules.

The existing systems to measure activation or inhibition of the activated SHH/PTCH pathway, are based on cell lines from human or mouse origin. Theses cells can schematically be classified in two categories destined to measure i-) endogenous cellular events after treatment; these events include triggering of a differentiation process and modulation of gene expression, notably of those genes known as transcriptional targets of pathway activation; ii-) cell lines engineered to report pathway activation/inhibition after transient or permanent introduction of reporter constructs made of responsive DNA driving a reporter gene. Cell lines developed so far are:

Human normal primary keratinocytes and fibroblasts in reconstructed skin where expression of GLI1 and GLI2 mRNA have been measured to demonstrate inhibition by the small Robotnikinin molecule of SHH/PTCH pathway activation by SHH (Stanton et al. 2009).

Healthy human primary keratinocytes from patients with nevoid basal cell carcinoma or Gorlin syndrome have been isolated to mimic the somatic loss of one PATCHED allele in sporadic BCC epidermal cells (Brellier et al., 2008a).

However, the above described cell lines have some disadvantages. Most of cell lines are not stable in the sense that after several passages the inserted genes expression decrease strongly or is shut down. Either those cell lines are not sufficiently robust to be efficient and sensitive to be used in a drug screening as a model. None of the cited prior art provides a system to allow a simple detection of activation in human epidermal keratinocytes.

Thus, there is a need for developing a human cell line easy to produce and to use, efficient, being a relevant model and sensitive for the screening or assessment of molecules libraries.

The inventors have developed a new cell line providing strong advantages. Indeed, the present invention provides an immortalized cell line of human keratinocytes with a natural exogene sequence bearing GLI binding sites in a reporter cassette which expression is stable overtime, particularly even after a high rate from passages in tissue culture.

Figure 6:
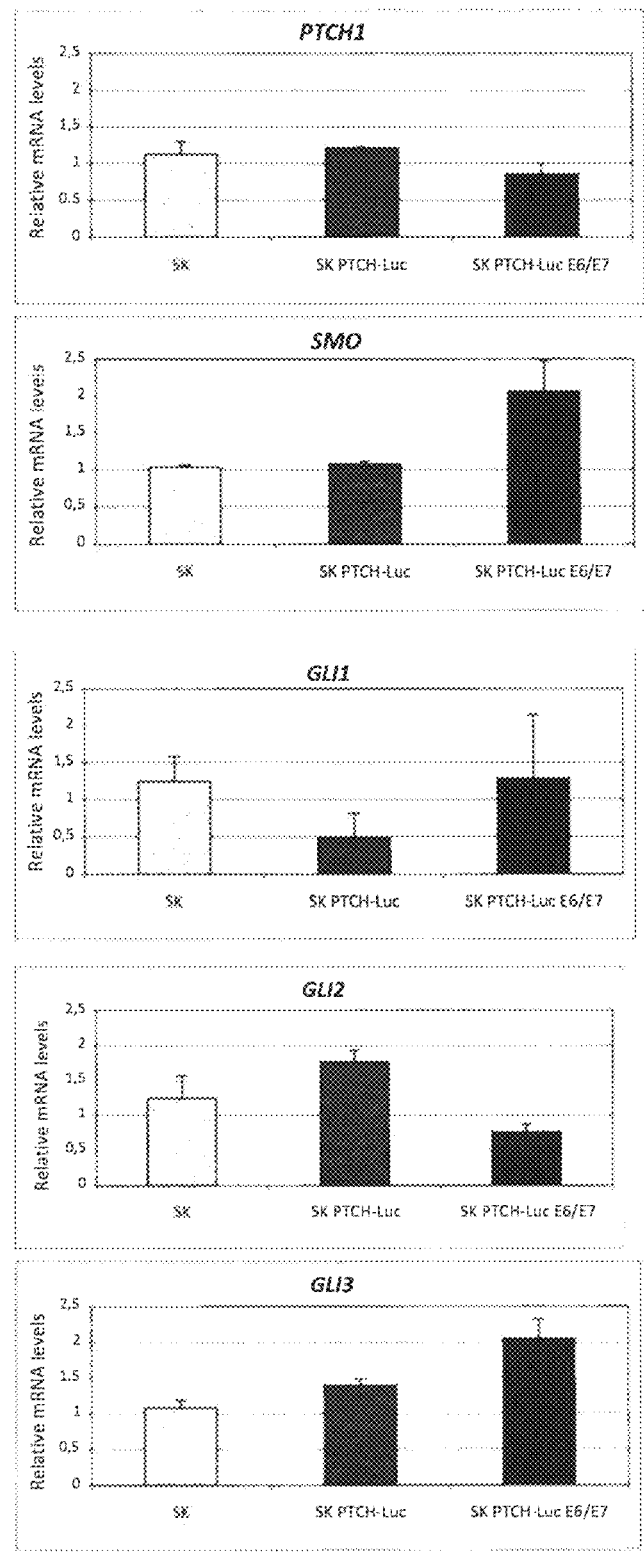

In preferred embodiment of invention, the reporter cassette is a PTCH1-luciferase construct. In hence, the immortalized keratinocytes cell line according to the invention, express the PTCH1 protein and/or other members of the pathway that are necessary to convey responses to agonists and antagonists of the said pathway as shown in FIG. 6. Said cell line is immortalized by retroviral transduction of pLE6/E7SN. In addition, this cell line is produced in the absence of serum and without using feeder cells.

The invention provides also a process for obtaining immortalized human keratinocytes as describe above, comprising the following steps:
- isolated human primary keratinocytes from healthy individual
- insert regulation region of PTCH1 upstream the reporter gene in appropriate plasmid by retroviral transduction
- select cell line expression with a medium of selection
- immortalized cell line by retroviral transduction with pLE6/E7SN
- select cell line expression with a medium of selection The invention provides also a drug screening method, wherein said immortalized keratinocytes cell line as described above is used to screen. In a preferred embodiment of the invention, the drug screening method comprises the following steps:
a). bringing one samples of immortalized cell line as described above into contact with one or more of the test compounds; b). measuring the expression or the activity of reporter gene and/or the activity of at least PTCH1 promoter thereof,
c). selecting the compounds for which a modulation of the expression or of the activity of a reporter gene and/or modulation of the expression of the gene PTCH 1 thereof, is measured in b) and compared with no drug mixture. In a preferred embodiment, the bioluminescence such as luciferase reporter gene or fluorescence is used.

In a preferred embodiment, the drug identified and or selected according to the drug screening method as described above is an anti-tumor drug.

The present invention also provides an In vitro method for the screening of candidate compounds for the preventive and/or curative treatment of cutaneous cancer and preferentially basal cell carcinoma.

The invention regards also to a drug obtainable with the drug screening method as described above.

DETAILED DESCRIPTION

Basal Cell Carcinomas (BCC) of the skin is the commonest human cancer. BCCs derive from epidermal keratinocytes. The great majority of BCCs occurs on photo-exposed skin due to ultraviolet induced mutagenesis. The steadily rising incidence of BCCs in the last decades is attributed to increasing enthusiasm for recreational sun exposure. Although BCC rarely metastasize, they can result in local destruction and invasion of underlying tissues and consequently, life threatening complications. BCC are usually treated by local surgical excision, topical chemotherapy, photodynamic therapy, but, according to tumor size, location and frequency, there may be considerable aestetic sequelae. Thus, drawbacks of current BCC treatments strongly support the need for pharmacological innovations that should specifically target the SONIC in so far as inappropriate and constitutive activation of this pathway is associated with the vast majority of BCC (see below). Furthermore, molecules that target the SHH pathway could also be of interest in the treatment of other/non-BCC cancer conditions (or their stromal cells) (melanoma, pancreas, oeasophagus, liver, prostate, lung, muscle, colon) where the SONIC HEDGEHOG/PATCHED (see below) has also been found inappropriately activated (Scales and de Sauvage, 2009).

The SHH/PATCHED Pathway

The SHH/PTCH signaling pathway is essential during embryogenesis and development where it controls cell fate by modulating proliferation and differentiation. Animal models, notably the fruit fly *drosophila melanogaster*, have shown that at specific stages of development, some cells produce and emit a signal, the Hedgehog molecule (HH), which, in turn, is received by target cells. In vertebrates, the family of Hedgehog molecules is composed of Sonic Hedgehog, SHH, Desert Hedgehog, DHH, and Indian Hedgehog, IHH. Target cells (of these ligands) express PATCHED (PTCH), a putative twelve pass transmembrane protein acting as the receptor of HH molecules. When HH molecules are not expressed and/or not secreted at the vicinity of target cells, PTCH acts as a repressor of the pathway by inhibiting another transmembrane protein called SMOOTHENED (SMO). SMO is a putative seven pass transmembrane protein apparented to G-protein coupled receptors. The inhibition of SMO by PTCH is relieved in the presence of HH molecules bound to PTCH. De-repression of SMO leads to activation of transcription factors of the GLI family (named GLI 1, 2 and 3) that activate (GLI1 and 2) or repress (GLI3), the transcription of their target genes. Interestingly, PTCH1 is a transcriptional target of GLI1 and GLI2 factors.

The importance of the SHH/PTCH pathway is illustrated by severe diseases due to mutations affecting its integrity at different levels. Notably, in the human, heterozygous mutations in the PTCH1 gene are responsible for the dominantly inherited genetic syndrome called nevoid basal cell carcinoma syndrome (NBCCS or Gorlin syndrome). NBCCS patients are highly prone to BCCs that generally (about 50% cases) present with a loss of heterozygosity in the PTCH1 locus. In Gorlin patients, more than 50% BCCs also bear mutation in the tumor suppressor gene TP53, suggesting some cooperation of the P53 and the SHH/PTCH pathways toward development of BCCs. Very interestingly, the two PTCH1 alleles are also lost in most sporadic (general population) BCCs; in the latter case, again, the two TP53 alleles are found mutated in 10 to 50% sporadic BCCs. 20-30% sporadic BCCs are mutated in both TP53 and PTCH1. In both NBCSS and sporadic BCCs, inactivation of PTCH results in constitutive activation of the pathway with accumulation GLI1 and GLI2 mRNAs.

The implication of the SHH/PTCH pathway activation in several cancer conditions, most notably in BCCs, has motivated much effort to set up experimental systems to assess the inhibitory activity of small molecules.

The existing systems of activity measure are based on cell lines from human or mouse origin. Theses cells can schematically be classified in two categories destined to measure i-) endogenous cellular events after treatment; these events include triggering of a differentiation process and modulation of gene expression, notably of those genes known as transcriptional targets of pathway activation; ii-) cell lines engineered to report pathway activation/inhibition after transient or permanent introduction of reporter constructs made of responsive DNA driving a reporter gene. Cell lines developed so far in the prior art reveals that none of those system allows simple detection of activation in human epidermal keratinocytes.

To provide a simple detection system, the inventors have worked to develop a human cell line in the respect of the following specifications (i.e. what we need for easy, efficient, relevant, sensitive assessment of molecules libraries):
  human cells,
  epidermal cells,
  growth in standard medium,
  needing no feeders,
  stably transformed by a relevant reporter sequence,
  genetic stability of the reporter cassette over a long period of time
  functional stability of the reporter cassette over a long period of time, which long term expression over cell generations;
  highly sensitive of activation; the cell line must report activation at doses closed to ligand (SHH) affinity, thus at the nM order.

To fulfil these specifications, the strategy was to use a human cell strain derived from normal human epidermis (Otto et al., 1999) stably transformed by a natural sequence able to drive expression of the Firely luciferase reporter gene. As indicated in prior art, no such line is available, neither from academic nor from commercial sources. The rationale of using natural SHH-responsive sequence stems from i-) the physiological relevance, i.e. good sensitivity, ii-) avoiding the use of direct tandem repeats of GliBS (n=8) upstream the Firely luciferase gene as described (Sasaki et al., 1997). Direct tandem repeats of GliBS are known to be very unstable; as in many other laboratories, all attempts to construct a reporter cell line using these sequences have failed. Concerning the easiness of growth and the independency toward feeder cells, we decided to abrogate or at least to attenuate, the expression of the tumor suppressor gene TP53. Indeed, it is known for instance, that HaCat cells (that derive form an epidermal carcinoma with the two TP53 allele mutated (Lehman et al., 1993)), are capable of growing in the absence of feeders cells. However, as explained below, use of these cells is not necessarily appropriate to measure pathway activation.

Previous work from the laboratory showed that P53 stabilisation after a single UVB irradiation is higher and prolonged in NBCCS compared to control keratinocytes (Brellier et al., 2008b). Also, report by Stecca and Ruiz-i-Altaba revealed mutual inhibition of Gli1 and P53 (Stecca and Ruiz i Altaba, 2009). Together with molecular epidemiology studies (showing mutations in both TP53 and PATCHED, in 20-30% BCCs), these results convergently indicate interaction between the P53 and the SHH/PTCH pathways.

Thus, it is reasoned that abrogation or attenuation of the P53 pathway using E6-E7 oncogenic proteins of Human Papilloma Virus 16 (HPV16) would favor activation of the SHH/PTCH pathway in human epidermal keratinocytes. It must also be emphasized that, although they are generally mutated in TP53, keratinocytes from squamous cell carcinoma (SCC) are never mutated in PTCH1 or at least do not show activation of the pathway (accumulation of target genes transcripts). This observation suggest that the SHH/PTCH pathway is not active in cells at the origin of SCCs (a subpopulation of epidermal stem cells). In spite of their easy growth in culture, SCC cells (such as HaCat cells) would thus not constitute appropriate recipient cells for reporter constructs. Preferably, it was decided to use human primary keratinocytes transformed with the E6-E7 oncogenic proteins.

Thus, the present invention provides an immortalized cell line of human keratinocytes with a natural exogenous sequence bearing GLI binding sites in a reporter cassette which expression is stable overtime, particularly even after a high rate from passages in tissue culture.

It is meant by stable expression of exogenous sequence bearing GLI binding sites in a reporter cassette overtime that after a high number of passages the level expression is the same as the initial level without recombination or loss of chromosomal material.

In preferred embodiment of invention, the reporter cassette is a PTCH1-luciferase construct. FIG. 1 provides an example of such a construct, which is the preferred reporter cassette although other reporter genes can be used in the context of the invention.

The immortalized keratinocytes cell line of according to the invention express the PTCH protein. Said cell line is immortalized by retroviral transduction. The skilled in the art is familiar with retroviral transduction techniques and all of them are applicable to the present invention. Any kind of retrovirus can be used such as Moloney murine leukemia virus (MoMLV), lentivirus, Eptein-Barr virus (EBV) . . . MoMLV is preferred for high performance of infection in human primary keratinocytes (Bergoglio et al., 2007). The retroviral transduction of pLE6/E7SN is preferred in this context.

In addition, this cell line is produced in the absence of serum and without using feeder cells which provides a greater benefit in terms of feeding and growth time. Indeed, serum or feeder cells can incorporate or secrete substances which can by their presence interfere or modify the activity response. Cells are grown in a definite medium providing the advantage of growing cells in medium which does not interfere with activity response. The invention provides thus a robust model with expected or calibrated response which avoids any interfering factors.

The invention provides also a drug screening method, wherein said immortalized keratinocytes cell line as described above is used to screen. The invention relates to an in vitro screening method of PTCH 1 inhibitors for treating skin cancer and preferably BCC, comprising determining the capacity of said drug to inhibit or down regulate expression or biological activity of PTCH.

In a preferred embodiment of the invention, the drug screening method comprises the following steps:

a). bringing one samples of immortalized cell line as described in claim 1 into contact with one or more of the test compounds;

b). measuring the expression or the activity of reporter cassette and preferably luciferase expression and/or the activity of at least PTCH 1 promoter thereof, c). selecting the compounds for which a modulation of the expression or of the activity of a reporter gene and/or modulation of the expression of the gene PTCH 1 thereof, is measured in b) and compared with no drug mixture.

In the context of the invention, any reporter gene can be used, such as beta-Gal, GFP, GFP derivatives, luciferase etc., reported with fluorescence or bioluminescence methods known by the skilled artisan. In a preferred embodiment, the reporter gene is luciferase.

The present invention provides tools for selecting SHH/PTCH pathway modulators. Those modulators are activators or inhibitors.

In a preferred embodiment, the drug identified and/or selected according to the drug screening method as described above is an anti-tumor drug. The reporter cassette is first activated and inhibition efficacy of one or several drug candidates (isolated or in a mixture) is assessed, preferably with increasing concentration. The examples provide an illustration with a particular embodiment in luciferase activity reporter model.

In another embodiment, the present invention provides an in vivo tool for assessing reporter gene activity in a humanised animal model (such as mouse or mini-pig) having said SK PTCH1 Luc E6 E7 immortalised cell line to follow drug candidate kinetic. The in situ assessment provides a considerable advantage with the bioluminescence or fluorescence as the effect of drug candidate is eye visible and does not require further read out methods. This tool is also usable with reconstructed epidermis or skin.

The examples which follow will illustrate the invention without limiting the scope thereof.

FIGURES

FIG. 1: Schematic drawing of the PTCH1-Luc proviral construct. LTR5', long terminal repeat 5'; encapsidation sequence; PTCH1 promoter, 4,4 kb 5' regulatory sequence of the human PTCH1 gene; Luc, Firely luciferase reporter gene; LTR 3', long terminal repeat 3'.

Figure 2:

FIG. 2: Schematic map of the LE6E7 SN proviral construct. E6E7, sequence of the human papilloma virus 16 encoding the E6 and E7 transforming proteins.

Figure 3:

FIG. 3: western blot analysis of the expression of the P53 protein in the indicated cells. GAPDH is a control of loading attenting that similar amount of protein is present in each lane.

Figure 4:
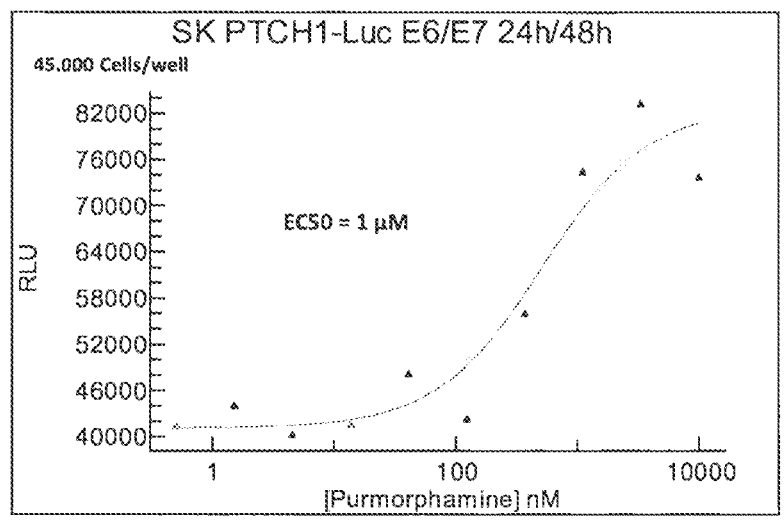

FIG. 4: Activation of the luciferase activity by purmorphamine in SK PTCH1-Luc E6/E7 cells. RLU: Relative Light Units. EC50 50% effective concentration.

Figure 5:
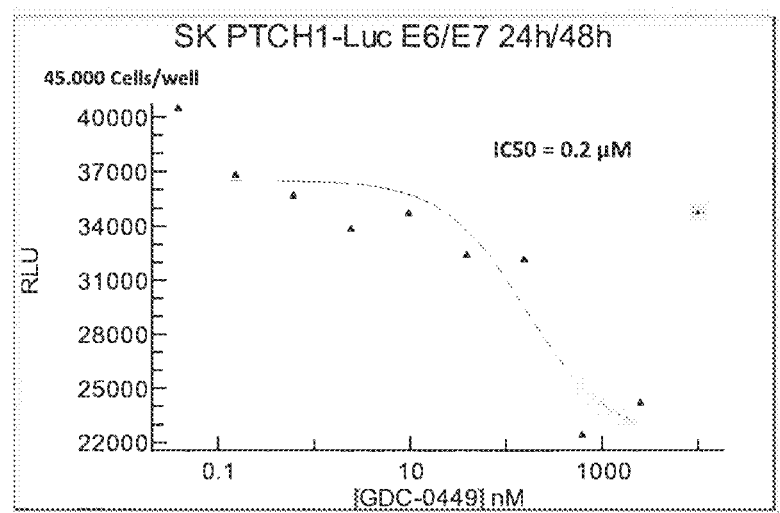

FIG. 5: Inhibition of the activation of the luciferase activity by GDC-0449 in SK PTCH1-Luc E6/E7 cells in the presence of purmorphamine. IC50, 50% Inhibitory concentration FIG. 6: SK PTCH1-Luc E6/E7 keratinocytes express essential actors of the PTCH/SHH pathway. RT-Q-PCR was performed from total cDNAs prepared from the indicated cells. SK human primary epidermal keratinocytes before or, after pLNeo-PTCH-Luc transduction, and subsequent E6/E7 immortalization by pLE6E7 retroviral transduction, SK PTCH-Lu E6/E7.

EXAMPLES

Example 1: Obtention of Immortalized Human Cell Line of Keratinocytes

This example describes the process for obtaining a valuable cell line model.

Materials and Methods

Cell Culture

Human primary keratinocytes (named SK) were isolated from a healthy non photo-exposed skin biopsy of a control patient (Otto et al., 1999).

The 4.4 kb 5' regulatory region of PTCH1 was inserted upstream of the Firefly luciferase reporter gene (Brellier et al., 2004) and cloned in pLNSX MoMLV retroviral backbone resulting in the p-Neo-PTCH1-Luciferase construct. Retroviral particles were produced by triple co-transfection of the plasmid with helper constructs bearing the Gag-Pol and Env MoMLV genes (titer>106 pfu/ml) as shown in FIG. 1.

Cells were transduced by retroviral supernatant. 48 hours following infection, cells were placed under selection pressure using 200 µg/ml of G418 for 8 days resulting in the SK PTCH1-Luc keratinocyte strain. The human PTCH1 5' regulatory sequence contains natural binding sites (how many) for the GLI transcription factors named GLIBS (GLI Binding Sites), sequence: 5-GACCACCCA-3', located at nucleotide 1748 and 2067 as described in (Brellier et al., 2004). The response of the reporter construct was verified by transient transfection of a GLI1 expression vector in the SK PTCH1-Luc human keratinocyte strain.

G418 is an aminoglycoside antibiotic similar in structure to gentamicin B1, produced by *Micromonospora rhodorangea*. G418 blocks polypeptide synthesis by inhibiting the elongation step in both prokaryotic and eukaryotic cells. Resistance to G418 is conferred by the Neomycin resistance gene (neo) from Tn5 encoding an aminoglycoside 3'-phosphotransferase, APH 3' II.

Selection in mammalian cells is usually achieved in three to seven days with concentrations ranging from 200 to 1000 µg/ml (Arnaudeau-Bégard et al., 2003).

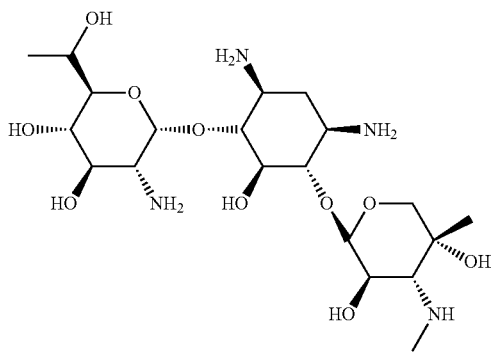

Chemical Structure of the G418 Antibiotic

The SK PTCH1-Luc keratinocyte cell line was then immortalized by retroviral transduction with pLE6/E7SN resulting in SK PTCH1-E6-E7 (FIG. 2) (Halbert et al., 1991, 1992). SK PTCH1-Luc E6/E7 were grown at 37° C. in a humified atmosphere containing 5% CO2. Serum free medium (SFM Gibco ref: 10725-018), contained 0.1 mM $CaCl_2$, $2.10^{-4}$ ng/ml EGF, 50 U/ml penicillin, 50 µg/ml streptomycin, 0.125 µg/ml amphotericin B.

Small Molecules Modulators of the SHH/PTCH Pathway

Purmorphamine (SMO agonist) and GDC-0449 (SMO antagonist) were diluted in DMSO at stock concentrations of 50 mM and 10 mM, respectively. To avoid side effects and toxicity, the final concentration of DMSO was fixed to 0.1% DMSO.

Lysis buffer and luciferase reagents were from the Steady-Glo® Luciferase Assay System kit (Promega, #E2520). Plates were read on a spectrophotometer (TopCount, Perkin Elmer).

Transformation of the SK-PTCH1-Luc Keratinocyte Cell Line by the E6/E7 Oncoproteins Effective transformation of the SK-PTCH1-Luc cell line was assessed by analysing its growth properties and attenuation of expression of the P53 tumor suppressor protein. FIG. 3 shows a western blot analysis of P53 in cell extracts prepared from preconconfluent (about 80%) primary epidermal keratinocytes (SK), primary epidermal keratinocytes (SK) after transformation using the E6E7 encoding retroviral vector (SK E6/E7), primary epidermal keratinocytes (SK) after transduction using the PTCH1-luc retroviral vector (SK PTCH1-Luc) h and after retroviral transformation using E6E7 retroviral construct (SK PTCH1-LUC E6/E7). The western blot shows the drastic decrease in the amount of the P53 protein.

Example 2: Experimental Conditions to Measure Activation/Inhibition of the SHH/PTCH Pathway in Human Epidermal Keratinocytes The aim of this example is to set up the conditions to measure activation and inhibition of the Patched pathway in human SK PTCH1-Luc E6/E7 keratinocytes and check if this cell model respond to activation by an agonist (purmorphamine) and to inhibition of the activation by an antagonist (GDC-0449) of the SHH/PTCH signaling pathway.

Experimental conditions of activation using SMO agonist of the PTCH1-Luc-E6 E7 reporter cells were first set up for optimisation. The SK PTCH1-Luc E6/E7 cells were plated in 96-well at various densities (5000 to 50000 cells/well) in opaque plates (Greiner, ref: 655083). In parallel, in order to follow cell growth, confluency, and lysis, the cell line was also seeded in transparent 96 wells plates (Greiner 655098). Serial dilutions of purmorphamine were prepared (0.2 nM<Conc.<50 µM). Results were matched with EC50 and IC50 values obtained in the SHH-Light II cell line. By doing so, we concluded that cells had to be seeded at the density of 45.000 cells/well and cultured for 24 hours (i.e. up to confluency); at this density, treatment of cells for 48 hrs with increasing concentrations of purmorphamin revealed 2.5 µM as the effective concentration for 80% activation (EC80) (FIG. 4). For experiments of inhibition of activation ells were for 48 hours with 2.5 µM of purmorphamine (determined as the EC80) together with serial dilutions of SMO antagonist GDC-0449 (0.04 nM<Conc.<10 µM).

Measure of Activation/Inhibition of the PATCHED Pathway in the Human SK PTCH1-Luc E6/E7 Epidermal Keratinocytes Activation Once experimental conditions optimized, SK PTCH1-Luc E6/E7 cells were plated at 45.000 cells per well, culture for 24 hours then treated for 48 hours by serial dilutions of purmorphamine. Each condition was done in duplicate and the experiment was performed at least twice. SK PTCH1-Luc E6/E7 cells responded to activation of the SHH/PTCH pathway when treated with purmorphamine and the EC50 value was determined at 1 µM (FIG. 3).

Inhibition of Activation

Co-treatment of SK PTCH1-Luc E6/E7 cells with purmorphamine and GDC-0449 led to the inhibition of the luciferase activity (FIG. 5). Under these circumstances, the IC50 of GDC-0449 was determined at 0.2 µM.

CONCLUSIONS

We have developed an immortalized human cell line of keratinocytes that respond to activation by an agonist (purmorphamine) and inhibition of the activation by an antagonist (GDC-0449) of the SHH/PTCH signaling pathway. The EC50 and IC50 demonstrate the relevance of this new tool. SK PTCH1-Luc E6/E7 cells do not need to be cultured in the presence of feeder cells. They can be expanded in a simple defined medium and they can grow easily due to immortalization. This tool is used in high throughput screening (HTS) to evaluate the efficacy of anti-tumoral molecules specifically targeting inappropriate activation of the SHH/PTCH pathway occurring in BCC but also in numerous non BCC cancers such as. The cellular characteristics allow us to develop HTS screening with virtually no limitation in the numbers of analysed wells.

REFERENCES

Arnaudeau-Bégard, C., Brellier, F., Chevallier-Lagente, O., Hoeijmakers, J. H., Bernerd, F., Sarasin, A., and Magnaldo, T. (2003). Genetic correction of DNA repair deficient/cancer prone xeroderma pigmentosum group C keratinocytes. Hum Gene Ther 14, 983-996.

Bergoglio, V., Larcher, F., Chevallier-Lagente, O., Bernheim, A., Danos, O., Sarasin, A., Rio, M. D., and Magnaldo, T. (2007). Safe selection of genetically manipulated human primary keratinocytes with very high growth potential using CD24. Mol Ther 15, 2186-2193.

Brellier, F., Bergoglio, V., Valin, A., Barnay, S., Chevallier-Lagente, O., Vielh, P., Spatz, A., Gorry, P., Avril, M. F., and Magnaldo, T. (2008a). Heterozygous mutations in the tumor suppressor gene PATCHED provoke basal cell carcinoma-like features in human organotypic skin cultures. Oncogene 27, 6601-6606.

Brellier, F., Marionnet, C., Chevallier-Lagente, O., Toftgard, R., Mauviel, A., Sarasin, A., and Magnaldo, T. (2004). Ultraviolet irradiation represses PATCHED gene transcription in human epidermal keratinocytes through an activator protein-1-dependent process. Cancer Res 64, 2699-2704.

Brellier, F., Valin, A., Chevallier-Lagente, O., Gorry, P., Avril, M. F., and Magnaldo, T. (2008b). Ultraviolet responses of Gorlin syndrome primary skin cells. Br J Dermatol 159, 445-452.

Halbert, C. L., Demers, G. W., and Galloway, D. A. (1991). The E7 gene of human papillomavirus type 16 is sufficient for immortalization of human epithelial cells. J Virol 65, 473-478.

Halbert, C. L., Demers, G. W., and Galloway, D. A. (1992). The E6 and E7 genes of human papillomavirus type 6 have weak immortalizing activity in human epithelial cells. J Virol 66, 2125-2134.

Lehman, T. A., Modali, R., Boukamp, P., Stanek, J., Bennett, W. P., Welsh, J. A., Metcalf, R. A., Stampfer, M. R., Fusenig, N., Rogan, E. M., et al. (1993). p53 mutations in human immortalized epithelial cell lines. Carcinogenesis 14, 833-839.

Otto, A. I., Riou, L., Marionnet, C., Mori, T., Sarasin, A., and Magnaldo, T. (1999). Differential behaviors toward ultraviolet A and B radiation of fibroblasts and keratinocytes from normal and DNA-repair-deficient patients. Cancer Res 59, 1212-1218.

Sasaki, H., Hui, C., Nakafuku, M., and Kondoh, H. (1997). A binding site for Gli proteins is essential for HNF-3beta floor plate enhancer activity in transgenics and can respond to Shh in vitro. Development 124, 1313-1322.

Scales, S. J., and de Sauvage, F. J. (2009). Mechanisms of Hedgehog pathway activation in cancer and implications for therapy. Trends Pharmacol Sci 30, 303-312.

Stecca, B., and Ruiz i Altaba, A. (2009). A GLI1-p53 inhibitory loop controls neural stem cell and tumour cell numbers. EMBO J 28, 663-676.

The invention claimed is:

1. An immortalized cell line of human keratinocytes with a natural exogenous sequence bearing at least one GLI binding site comprising a 5'-GACCAACCCA-3' sequence (SEQ ID NO: 1) in a reporter cassette; and wherein the cell is produced in the absence of serum and without feeder cells.

2. The immortalized cell line of claim 1, wherein the expression of the reporter cassette is the same as an initial level without recombination or loss of chromosomal material.

3. The immortalized cell line of claim 1, wherein the reporter cassette is a PTCH1-luciferase construct.

4. The immortalized cell line of claim 3, wherein the cell line expresses a PTCH protein.

5. The immortalized cell line of claim 1, wherein the cell line is immortalized by retroviral transduction of pLE6/E7SN.

6. A process for obtaining immortalized human keratinocytes as described in claim 1, the process comprising the following steps of:

isolating human primary keratinocytes from a healthy individual, inserting a regulation region of PTCH1 upstream of a reporter gene in an appropriate plasmid, and immortalizing the cell line by retroviral transduction with pLE6/E7SN.

7. A drug screening method, the method comprising screening a capacity of a drug to inhibit or down regulate expression or biological activity of PTCH with the immortalized cell line of claim 1.

8. A drug screening method, the method comprising the following steps of:
   a. contacting one sample of the immortalized cell line of claim 1 with at least one test compound or a mixture of compounds,
   b. measuring expression or activity of a reporter gene and/or activity of a PTCH1 promoter, and
   c. selecting at least one compound for which a modulation of the expression or of the activity of the reporter gene and/or a modulation of the expression of the PTCH1 gene thereof is measured in step b) when compared to the expression or activity in the absence of any test compounds or mixture of compounds.

9. The drug screening method of claim 8 wherein the reporter gene is a luciferase or a GFP reporter gene.

10. The drug screening method of claim 7, wherein the method identifies an antitumor drug.

11. An In vitro method for screening candidate compounds for preventive and/or curative treatment of cutaneous cancer, the method comprising the following steps of:
   a. contacting one sample of the immortalized cell line of claim 3 with at least one test compound or with a mixture of compounds,
   b. measuring the expression or the activity of luciferase and/or the activity of at least one PTCH1 promoter thereof, and
   c. selecting at least one compound for which a modulation of the expression or of the activity of the reporter cassette and/or a modulation of the expression of the PTCH1 gene, is measured in step b) when compared to the expression or activity in the absence of any test compounds or mixture of compounds.

\* \* \* \* \*